(12) United States Patent
Lan-Hargest et al.

(10) Patent No.: US 6,562,995 B1
(45) Date of Patent: May 13, 2003

(54) DELTA DICARBONYL COMPOUNDS AND METHODS FOR USING THE SAME

(75) Inventors: Hsuan-Yin Lan-Hargest, Fallston, MD (US); Norbert L. Wiech, Phoenix, MD (US)

(73) Assignee: Beacon Laboratories, Inc., Phoenix, MD (US)

( * ) Notice: Subject to any disclaimer, the term of this patent is extended or adjusted under 35 U.S.C. 154(b) by 0 days.

(21) Appl. No.: 09/742,588

(22) Filed: Dec. 21, 2000

(51) Int. Cl.$^7$ ................................................ C07C 69/76
(52) U.S. Cl. ........................ 560/104; 560/152; 560/179; 560/205; 560/222; 560/105; 560/110; 560/128; 558/252; 564/201; 564/204; 564/215
(58) Field of Search ................................. 560/129, 147, 560/152, 179, 205, 222, 105, 110, 104, 128; 558/252; 564/201, 204, 215

(56) References Cited

U.S. PATENT DOCUMENTS

| | | |
|---|---|---|
| 3,282,784 A | 11/1966 | Gordon et al. |
| 4,611,002 A | 9/1986 | Ondetti |
| 4,774,256 A | 9/1988 | Delaney et al. |
| 5,055,588 A | 10/1991 | Takase et al. |
| 5,173,506 A | 12/1992 | Neustadt et al. |
| 5,200,553 A | 4/1993 | Nudelman et al. |
| 5,262,436 A | 11/1993 | Haslanger et al. |
| 5,411,987 A | 5/1995 | Wollweber et al. |
| 5,599,940 A | 2/1997 | Lantzsch et al. |
| 5,612,371 A | 3/1997 | Danvy et al. |
| 5,626,855 A | 5/1997 | Philippe |
| 5,667,962 A | 9/1997 | Brunengraber et al. |
| 5,710,176 A | 1/1998 | Rephaeli et al. |
| 5,710,279 A | 1/1998 | Lantzsch et al. |
| 5,880,152 A | 3/1999 | Tung et al. |
| 5,939,455 A | 8/1999 | Rephaeli |
| 6,040,342 A | 3/2000 | Rephaeli et al. |
| 6,071,923 A | 6/2000 | Nudelman et al. |
| 6,110,955 A | 8/2000 | Nudelman et al. |
| 6,110,970 A | 8/2000 | Nudelman et al. |
| 6,162,811 A | 12/2000 | Guillonneau et al. |

FOREIGN PATENT DOCUMENTS

| | | |
|---|---|---|
| EP | 0850940 B1 | 7/1998 |
| WO | WO 98/29114 | 7/1998 |
| WO | WO 98/39965 | 9/1998 |
| WO | WO 99/29705 | 6/1999 |
| WO | WO 00/17162 | 3/2000 |

OTHER PUBLICATIONS

A. A. Kirchanov et al, "Synthesis of α-(acyloxy)ketones", Chemical Abstracts 95:219751 [Izv. Akad. Nauk SSR, Ser. Khim. (1981) pp. 1914–1915]*

* cited by examiner

*Primary Examiner*—Paul J. Killos
(74) *Attorney, Agent, or Firm*—Fish & Richardson P.C.

(57) ABSTRACT

Amidomethyl esters, carbonylmercaptomethyl esters, keto-containing esters, amidomethyl thioesters, amidomethyl amides, and methylene dithioesters are disclosed. The novel compounds have two carbonyl groups connected by a linking moiety having an oxygen, sulfur or nitrogen attached to a methylene group, to which is further attached a sulfur, nitrogen or $CH_2$ group. Methods of treating illnesses and conditions, such as cancer, hemological disorders, inherited metabolic disorders and others, using these compounds are also disclosed.

12 Claims, 10 Drawing Sheets

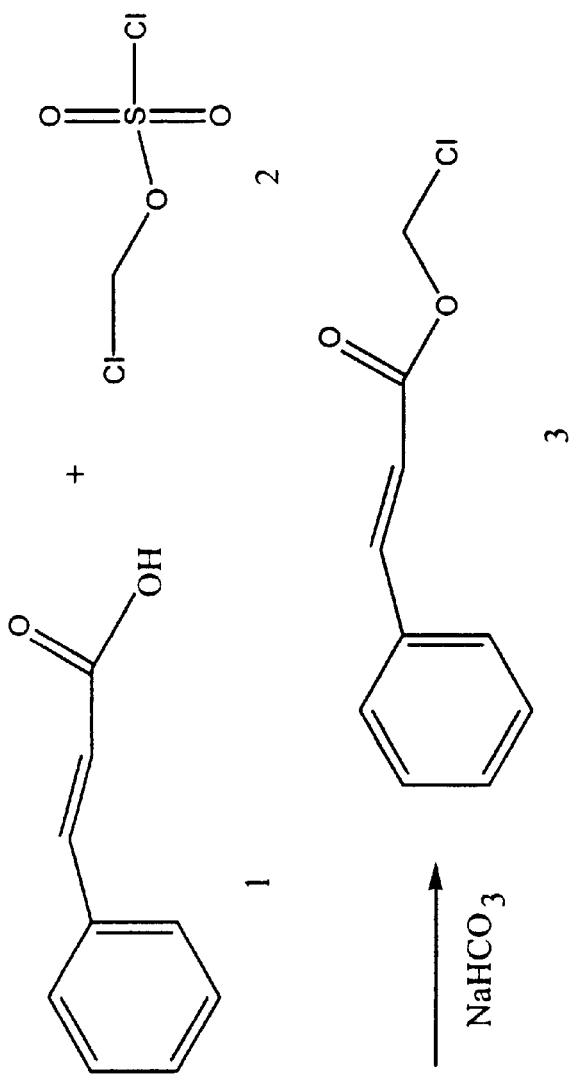
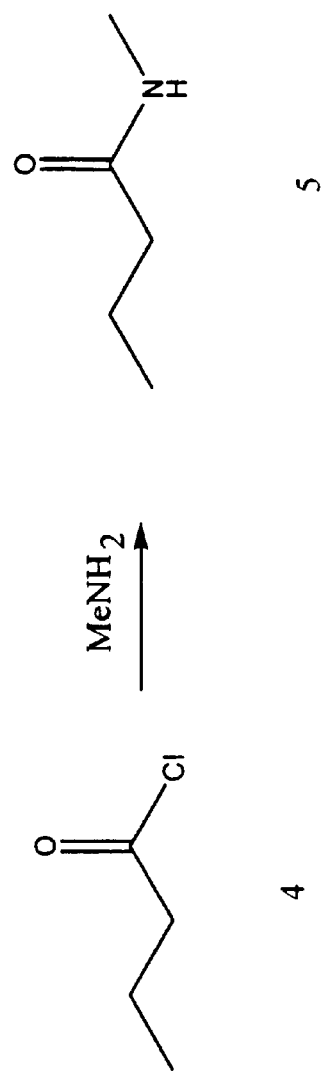
Figure 1A
Figure 1B

US 6,562,995 B1

DELTA DICARBONYL COMPOUNDS AND METHODS FOR USING THE SAME

FIELD OF THE INVENTION

The present invention relates to delta dicarbonyl compounds in which the two C=O groups are linked by a moiety having three atoms, at least one of which is a heteroatom. The invention further relates to methods for using these compounds in the treatment of cancer and other proliferative diseases, hemoglobinopathies and inherited metabolic disorders and to treat or alleviate various other illnesses and conditions, such as by hematopoietic stimulation. The present invention also relates to methods for using the disclosed compounds in the inhibition of histone deacetylase.

BACKGROUND INFORMATION

Histones are unique proteins in the nucleus of a cell. DNA is wound around a complex of histones to form nucleosomes. As such, histones are an integral structural element of the chromatin material. The histones complexed with the DNA are susceptible to a range of chemical modifications, one of which is acetylation, and the reverse of which is deacetylation. Acetylation of histone protein is believed to facilitate transcription of the DNA, thereby enhancing gene expression. Histone deacetylase is believed to reverse the process that represses gene expression. Histone dynamics are regulated by two enzymes—histone acetyl transferase and histone deacetylase.

Hyperacetylation due to inhibition of histone deacetylation, and the resulting expression of a latent gene, have been observed or proposed to occur in numerous inherited metabolic diseases and in cancer. The inhibition of histone deacetylase is believed to activate an otherwise dormant fetal gene, which serves as a redundant or back-up gene. Pharmacological inhibition of histone deacetylase, therefore, is believed to induce the expression of repressor genes in cancer tissue, inhibit the expression of tumor-promoting genes, and induce the expression of the redundant or back-up gene in patients suffering from various metabolic and hematological diseases. Thus, inhibition of histone deacetylase is proposed to slow the growth of neoplastic cells and/or reverse the deficient process of various metabolic and hematological diseases. Inhibition of histone deacetylase is also believed to play a role in antiprotozoal activity.

Trichostatin is the most potent inhibitor of histone deacetylase observed so far, but due to various drawbacks, such as availability of the material, has not been pursued.

Butyric acid is a natural product that has been known for several decades to be an effective differentiating and antiproliferative agent in a wide spectra of neoplastic cells in vitro. For example, butyric acid has been reported to induce cellular and biochemical changes in cancer cells, to induce apoptosis, and to increase the expression of transfected DNA, although the mechanism of action of butyric acid is unknown. Increased histone acetylation following treatment with butyric acid has been correlated with changes in transcriptional activity and at differentiated states of cells. Butyric acid and its salts, however, have shown low potency in both in vitro assays and clinical trials, and thus require large doses to achieve even minimal therapeutic effects. This can lead to fluid overload and mild alkalosis.

The present invention is directed to dicarbonyl compounds, and methods for using the same, that have also been found to inhibit histone deacetylase. The present compounds show significantly greater activity than butyric acid or its salts. That compounds containing the dicarbonyl moiety of the present invention have the ability to inhibit histone deacetylase has been previously unreported in the art.

SUMMARY OF THE INVENTION

The present invention relates to novel dicarbonyl compounds having a unique moiety linking the two carbonyl groups. The linking moiety contains an oxygen, sulfur or nitrogen atom attached to a carbon atom; attached to the opposite end of the carbon atom is either a sulfur, a nitrogen, or another carbon atom. The compounds are useful in the inhibition of histone deacetylase, among other things.

The present invention therefore further relates to methods of treating a patient for an illness, particularly wherein the illness is one in which histone deacetylase inhibition would be beneficial. Examples include cancer, hemoglobinopathies and inherited metabolic disorders. Other illnesses and conditions that can be treated according to the present invention are discussed herein. In the case of histone deacetylase inhibition, the present compounds are believed to function by chelating the zinc ion at the active site of histone deacetylase; the inventor does not wish to be bound by this mechanism, however.

It is therefore an aspect of the invention to provide dicarbonyl compounds having a linking moiety comprising at least one heteroatom.

Another aspect of the invention provides methods for treating a patient sing the present dicarbonyl compounds.

A method for inhibiting histone deacetylase in a patient is also an aspect of the present invention.

These and other aspects of the invention will be apparent upon reviewing the attached specification and appended claims.

BRIEF DESCRIPTION OF THE FIGURES

FIGS. 1A, 1B and 1C show a reaction scheme for preparing N-methylbutyramidomethyl cinnamate according to Example 1.

DETAILED DESCRIPTION OF THE INVENTION

Figure 1C:
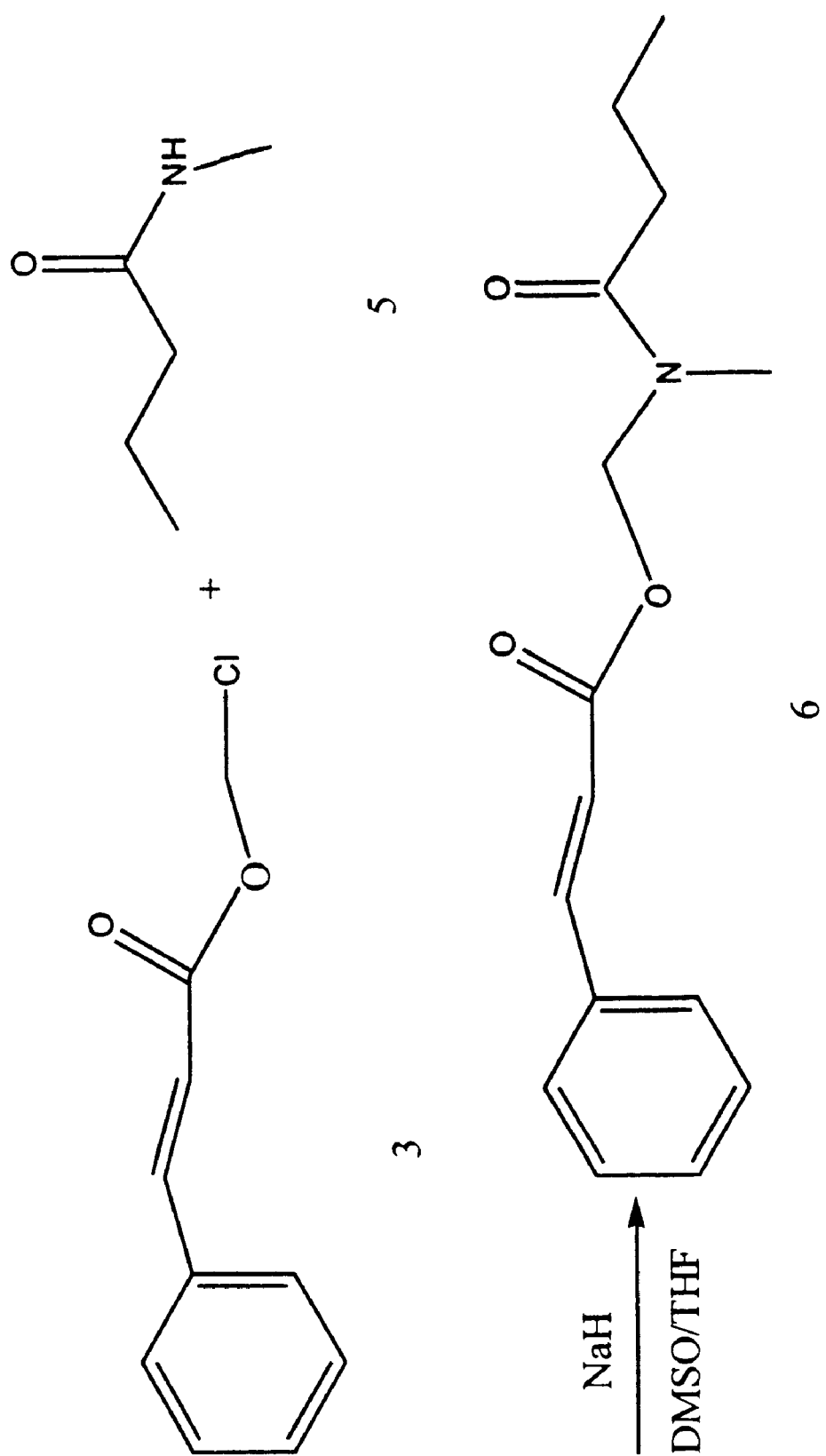

The present invention is directed to compounds having the general formula (1):

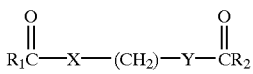

$$R_1C(=O)-X-(CH_2)-Y-CR_2(=O) \quad (1)$$

wherein X is selected from the group oxygen, sulfur and N(R);

wherein Y is selected from the group sulfur, N(R), and CH$_2$;

wherein R is either H or CH$_3$;

wherein R$_1$ and R$_2$ are the same or different and have the general formula (2):

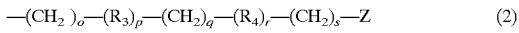

$$-(CH_2)_o-(R_3)_p-(CH_2)_q-(R_4)_r-(CH_2)_s-Z \quad (2)$$

wherein R$_3$ and R$_4$ are the same or different and are selected from the group (CH=CH), (C≡C), sulfiirand oxygen;

wherein Z is selected from the group consisting of hydrogen, and substituted or unsubstituted aryl, heteroaryl, cycloalkyl having the formula C$_n$H$_{2n-1}$, and alkoxy;

wherein n is 3 or greater; and wherein o, p, q, r and s are the same or different and are each between 0 and 10.

When X and Y are both sulfur, a methylene dithioester is presented; when X is sulfur and Y is N(R), or when X is N(R) and Y is sulfur, an amidomethyl thioester is presented; when X and Y are both N(R), an amidomethyl amide is presented; when X is oxygen and Y is sulfur, a carbonylmercaptomethyl ester is represented; when X is oxygen and Y is N(R) an amidomethyl ester is represented; and when X is oxygen and Y is CH$_2$ a keto-containing ester is represented. The present invention is therefore directed to novel compounds having a three-atom linkage comprising one or more heteroatoms linking two carbonyl groups.

When X and Y is N(R), R is preferably methyl.

For each of R$_1$ and R$_2$, the aliphatic chain contains a substituent, represented in formula 2 above by "Z". The Z substituent can be a hydrogen atom or can be an aryl, heteroaryl, cycloalkyl of formula C$_n$H$_{2n-1}$ or alkoxy group; when Z is something other than hydrogen, it can be optionally substituted with one or more substituents selected from halogen, including fluorine, chlorine, bromine and iodine, hydroxy, alkyl, alkoxy, cyano, amino, nitro, carbonyl, halogenated hydrocarbon groups and other substituents as discussed below. A preferred halogenated hydrocarbon group is trifluoromethyl.

R$_1$ and R$_2$ both have the general formula 2 depicted above, but can be the same or different; thus R$_1$ and R$_2$ can each have different permeations of formula 2 within the same compound. Accordingly, R$_3$, R$_4$, the "Z" group and the values of n, o, p, q, r and s can be the same or different in each of the R$_1$ and R$_2$ groups.

Preferred embodiments of the above invention include those wherein both R$_1$ and R$_2$ are the same or different and are selected from the group comprising acetate, propionate, butyrate, pentanoate, hexanoate, heptanote and octanoate. Other preferred compounds include cinnamoyloxymethyl thiobutyrate and butyroyloxymethyl thiocinnamate, wherein X is oxygen, Y is sulfur, one of R$_1$ and R$_2$ is CH$_2$CH$_2$CH$_3$ and the other of R$_1$ and R$_2$ is —CH=CH—C$_6$H$_5$. Other preferred compounds include N-methylbutyramidomethyl cinnamate, wherein X is oxygen, Y is N (CH$_3$), R$_1$ is —CH=CH—C$_6$H$_5$, and R$_2$ is CH$_2$CH$_2$CH$_3$; a similar compound is N-methylcinnamamidomethyl butyrate, in which the R$_1$ and R$_2$ groups are switched. Another preferred compound is 3-oxohexyl cinnamate, in which X is oxygen, Y is CH$_2$, R$_1$ is —CH=CH—C$_6$H$_5$ and R$_2$ is CH$_2$CH$_2$CH$_3$. N-methyl-2-(2-methoxyethoxy)acetamidomethyl butyrate is also a preferred compound; in that compound, X is oxygen, Y is N(CH$_3$), R$_1$ is CH$_2$CH$_2$CH$_3$ and R$_2$ is CH$_2$OCH$_2$CH$_2$OCH$_3$. Yet another preferred compound is bis(thiobutyryl)methane, wherein X and Y are both sulfur and R$_1$ and R$_2$ are both CH$_2$CH$_2$CH$_3$.

As used herein, "aryl" includes any stable 5- to 14-membered monocyclic, bicyclic or tricyclic ring, containing at least one aromatic carbon ring, for example, phenyl, naphthyl, indanyl, tetrahydronaphthyl (tetralinyl) and the like. "Stable" as used herein refers to compounds that are sufficiently robust to survive isolation to a useful degree of purity from a reaction mixture. As noted above, one or more substituents on the aryl group are optional, and when present, the substitutents can be the same or different and can be halogen, alkyl, alkoxy, hydroxy, cyano, amino, nitro, carbonyl or halogenated hydrocarbon groups.

As used herein, the term "heteroaryl" includes any stable 5- to 14-membered monocyclic, bicyclic or tricyclic aromatic heterocyclic ring comprising carbon atoms and from 1 to 5 heteroatoms selected from the group consisting of N, O and S, wherein the nitrogen may optionally be quaternized; the term includes any bicyclic or tricyclic group in which a heteroaryl ring is fused to the other ring(s). The heteroaryl ring may be attached to its pendant group at any heteroatom or carbon atom that results in a stable structure. As with the aryl group, the presence of substitution on the heteroaryl group is optional; if present, the one or more substituents can be on a carbon atom or heteroatom so long as the resulting compound is stable and all the valencies of the atom have been satisfied. The one or more substituents on the heteroaryl group can be the same or different and are the same as those substituents listed above for the aryl groups; also included are alkylammonium salts when the substituent is an alkyl group attached to the nitrogen atom of the heteroaryl ring. These quaternized ammonium salts include halides, hydrohalides, sulfates, methanesulfates, toluenesulfates, nitrates, phosphates, maleates, acetates, lactates or any other pharmaceutically acceptable salt. Examples of heteroaryl groups include, but are not limited to, furanyl, thienyl, pyrrolyl, pyrazolyl, imidazolyl, tetrazolyl, benzofuranyl, benzothienyl, indolyl, indolenyl, quinolinyl, isoquinolinyl, benzimidazolyl, thiazole, thioxane, benzothiozole and benzothiazin.

As discussed above, either of the Z groups can be a cycloalkyl group having the general formula C$_n$H$_{2n-1}$ wherein n is 3 or greater; any stable cycloalkyl group having this general formula is therefore within the scope of the invention. Typically, "n" will not be higher than about 12. Again, the cycloalkyl can be unsubstituted or substituted with one or more of the substituents listed above. Similarly, Z can be an alkoxy group which is unsubstituted or substituted with one or more of the same substituents. "Alkoxy" will be understood by those skilled in the art as referring to an alkyl group having at least one oxygen substituent represented by R-O, wherein R is an alkyl group having between about 1 and 5 carbons.

The term "alkyl" is used herein to refer to branched or straight chain saturated aliphatic hydrocarbon groups. Unless indicated otherwise, the alkyl groups typically have 15 carbons or less.

Pharmaceutically acceptable salts of any of the above compounds are also within the scope of the invention. As used herein, "pharmaceutically acceptable salts" refer to derivatives of the disclosed compounds that are modified by making acid or base salts. Examples include, but are not limited to, mineral or organic acid salts of basic residues such as amines, alkali or organic base salts of acidic residues such as carboxylic acids, and the like. Pharmaceutically acceptable salts include, but are not limited to, hydrohalides, sulfates, methanesulfates, toluenesulfonates, nitrates, phosphates, maleates, acetates, lactates and the like.

Pharmaceutically-acceptable salts of the compounds of the present invention can be prepared by reacting the free acid or base forms of these compounds with a stoichiometric or greater amount of the appropriate base or acid in water or in an organic solvent, or in a mixture of the two; generally, nonaqueous media like ether, ethyl acetate, ethanol, isopropanol, or acetonitrile are preferred. The salts of the invention can also be prepared by ion exchange, for example. Lists of suitable salts are found in *Remington's Pharmaceutical Sciences*, 18$^{th}$ ed., Mack Publishing Company, Easton, Pa. (1990).

The present compounds have been found to be useful as antiproliferative agents; the compounds have also been found to inhibit histone deacetylase. Accordingly, the present invention is also directed to methods of treating illnesses in which proliferation of neoplastic or diseased cells occurs, or illnesses in which inhibition of histone deacetylase would be desired; as discussed above, inhibition of histone deacetylase results in the enhancement of gene expression that slows the growth of neoplastic cells and reverses the deficient process of various metabolic and hematological diseases. It will be understood that the present invention encompasses the treatment of various illnesses, as that term is defined herein, regardless of whether the treatment is through histone deacetylase inhibition, through another mechanism, or through a variety of mechanisms.

More specifically, the present invention is further directed to a method for treating an illness in a patient comprising administering to that patient an effective amount of a compound having formula 1. Illnesses treatable according to the present invention include, but are not limited to, various cancers, hematological diseases, and inherited metabolic diseases. Cancer includes, but is not limited to, leukemias, such as acute promyelocytic leukemia, acute myeloid leukemia, and acute myelomonocytic leukemia; other myelodysplastic syndromes; multiple myeloma such as breast carcinomas, cervical cancers, melanomas, colon cancers, nasopharyngeal carcinoma, non-Hodgkins lymphoma (NHL), Kaposi's sarcoma, ovarian cancers, pancreatic cancers, hepatocarcinomas, prostate cancers, squamous carcinomas, other dermatologic malignancies, teratocarcinomas, T-cell lymphomas, lung tumors, gliomas, neuroblastomas, peripheral neuroectodermal tumors, rhabdomyosarcomas, and prostate tumors and other solid tumors. Hematological diseases or hemoglobinopathies within the scope of the present invention include, but are not limited to, thalassemias, sickle cell anemias, infectious anemias, aplastic anemias, hypoplastic and hypoproliferative anemias, sideroblastic anemias, myelophthisic anemias, antibody-mediated anemias, anemias due to chronic diseases and enzyme-deficiencies, and anemias due to blood loss, radiation therapy and chemotherapy. Inherited metabolic diseases include, but are not limited to, Duschenne's muscular dystrophy, cystic fibrosis, and adrenoleukodystrophy. Thus, the term "illness" as used herein encompasses at least all of these things.

The term "illness" as used herein also encompasses various conditions such as cutaneous ulcers and gastrointestinal disorders. The cutaneous ulcers which can be treated in accordance with the current methods include leg and decubitus ulcers, stasis ulcers, diabetic ulcers and atherosclerotic ulcers. Gastrointestinal disorders treatable by the present methods include colitis, inflammatory bowel disease, Crohn's disease and ulcerative colitis. The term illness also refers to wounds such as abrasions, incisions, and burns.

"Illness" also encompasses treatment, prevention, or amelioration of virus-associated tumors including, but not limited to, EBV-associated malignancy, Kaposi's sarcoma, AIDS-related lymphoma, hepatitis B-associated malignancy or hepatitis C-associated malignancy. EBV-associated malignancy include, but are not limited to, nasopharyngeal carcinoma and non-Hodgkins' lymphoma. The present compounds can be administered in conjunction with a therapeutically effective amount of an antiviral agent such as ganciclovir, acyclovir and famciclovir. Protozoan infections are also included within "illness" and include, for example, malaria, cryptosporidiosis, trypanosomiasis, Eimeria sp., Plasmodium sp., toxoplasmosis, and coccidiosis.

In another embodiment of this invention, "illness" refers to alopecia, or hair loss. Alopecia is a common condition that results from diverse causes. In particular, alopecia frequently occurs in cancer patients who are treated with chemotherapeutic drugs and/or irradiation. Such agents damage hair follicles which contain mitotically active hair-producing cells. Such damage may cause abnormally slow growth of the hair or may lead to frank loss. Thus, the present invention further relates to methods for protecting against injury to hair follicles in a patient by administering one or more of the present compounds to the patient.

"Patient" refers to members of the animal kingdom, including but not limited to humans. Preferably, the methods of the present invention are applied to a patient suffering from any of the illnesses listed above.

The compounds of the invention can be administered by any conventional means available for use in conjunction with pharmaceuticals, either as individual therapeutic agents or in combination with other therapeutic agents known in the art for the illness being treated. The compounds can be administered alone, but are generally administered with a pharmaceutically acceptable carrier selected on the basis of the chosen route of administration and standard pharmaceutical practice. The compositions of the invention may be adapted for oral, parenteral, topical, transdermal, transmucosal, rectal or intranasal administration, and may be in unit dosage form; the term "parenteral" as used herein includes subcutaneous, intravenous, intramuscular, or intrasternal injection or infusion techniques. Methods for preparing the present compositions for use by a patient are well known to those skilled in the pharmaceutical arts; formulations can include one or more fillers or preservatives in addition to the active ingredient and carrier.

"Pharmaceutically acceptable carrier" includes any and all solvents, dispersion media, coatings, antibacterial and antifungal agents, isotonic and absorption delaying agents, and the like. The use of such media and agents for pharmaceutically active substances is well known in the art. Use of any of these media or agents is contemplated with the compounds of the present invention, absent compatibility problems with the active compound.

It is especially advantageous to formulate compositions in dosage unit form for ease of administration and uniformity of dosage. Dosage unit form as used herein refers to physically discrete units suited as unitary dosages for the patient to be treated, each unit containing a pre-determined quantity of active compound or "effective amount" calculated to produce the desired therapeutic effect in association with the pharmaceutical carrier. The specification for the dosage unit forms of the invention are dictated by and directly dependent on the characteristics of the active compound, the particular therapeutic effect to be achieved, and the limitations inherent in the art of compounding such an active compound for the treatment of sensitivity in individuals.

The appropriate dosage or "effective amount" administered in any given case will, of course, vary depending upon known factors, such as the pharmacodynamic characteristics of the particular compound and its mode and route of administration; the age, general health, metabolism, weight of the patient and other factors which influence response to the compound; the nature and extent of the illness being treated; the kind of concurrent treatment, if any; the frequency of treatment; and the effect desired. Generally, the effective amount will be that amount of the present compounds needed to bring about the desired level of histone deacetylase inhibition, without resulting in toxicity to the patient. A daily dosage of active ingredient will typically be between about 10 to 10,000 milligrams per meter$^2$ (mg/m$^2$) of body mass, with the preferred dose being 50–5,000 mg/m$^2$ body mass.

It will be appreciated that the therapeutic benefits of administration of the present compounds will be manifest in a variety of ways, depending on the patient and the illness being treated. More than one therapeutic benefit may be observed. The elicitation of any therapeutic benefit by the present methods is within the scope of the invention. "Treating" or "treatment" refers herein to both therapeutic and prophylactic treatments; for ease of reference, "therapeutic benefit" therefore refers collectively to both therapeutic and prophylactic benefits. Therapeutic benefits that may be achieved according to the present invention include, for example, one or more of retarding or eliminating tumor growth, apoptosis of tumor cells, healing wounds, healing cutaneous ulcers, ameliorating gastrointestinal disorders, modulating gene expression, inhibiting telomerase activity, inducing tolerance to antigens, preventing and/or ameliorating protozoan infection, inhibiting histone deacetylace in cells, modulating an immune response, ameliorating the effects of a cytotoxic agent, stimulating hematopoietic cells ex vivo, and protecting hair follicles.

Modulation of an immune response can include, for example, enhancing cytokine secretion, inhibiting or delaying apoptosis in polymorphonuclear cells, enhancing polymorphonuclear cell function by augmenting hematopoietic growth factor secretion, inducing expression of cell surface antigens in tumor cells, and enhancing progenitor cell recovery after bone marrow transplantation.

Ameliorating the effects of a cytotoxic agent involves administering the present compounds in conjunction with the cytotoxic agent in such an amount so as to induce growth arrest of rapidly-proliferating epithelial cells of the patient, thereby protecting them from the cytotoxic effects of the agent. Cytotoxic agents, include, for example, chemotherapeutic agents, anticancer agents, and radiation therapy.

Modulating gene expression can be used to enhance, augment or repress the expression of a gene of interest. When expression of the gene of interest is to be enhanced or augmented, the gene can encode a gene product that is or acts as a repressor of another gene, a tumor suppressor, an inducer of apoptosis or an inducer of differentiation. Enhancing recombinant gene expression can be effected in a number of cells; the gene product can be any protein or peptide of interest such as tumor suppression genes. When expression of the gene of interest is to be repressed, the gene can encode a gene product that is or acts as an oncogene or an inhibitor of apoptosis, such as the bcl2 gene.

Inhibition of telomerase activity in cancer cells inhibits the malignant progression of the cells.

Inducing tolerance to an antigen is preferably carried about with a self-antigen, such as those associated with an autoimmune disease such as systemic lupus erythromatosus, rheumatoid arthritis, multiple sclerosis or diabetes. Tolerance can also be induced to one or more antigens present on a transplanted organ or cells.

The present invention is also directed a pharmaceutical composition comprising the compound of formula 1 within a pharmaceutically acceptable carrier.

EXAMPLES

The following examples are intended to illustrate the invention, and should not be construed as limiting the invention in any way.

Example 1

Preparation of N-methylbutyramidomethyl cinnamate 6

Reference numerals correspond with those in FIGS. 1A, 1B and 1C.

In the preparation of N-methylbutyramidomethyl cinnamate 6, chloromethylcinnamate (CMC) 3 and N-methylbutyramide 5 were first prepared. Chloromethylcinnamate 3 was prepared as follows. To a mixture of cinnamic acid 1 (100 g) in water (700 mL) and methylene chloride (700 mL) containing 215.5 g of sodium bicarbonate, and 22.9 g of tetrabutylammonium hydrogen sulfate was added 128.1 g of chloromethylchlorosulfate 2 in 250 ML of methylene chloride at a rate to keep the temperature below 30° C. The addition required about one hour and there was vigorous gas evolution throughout the addition. The temperature peaked at the end of addition at 17.4° C. About one hour post addition, the gas evolution ceased. Two hours after addition was complete, an aliquot was concentrated in vacuo and analyzed by NMR and found to be complete. The layers of the reaction mixture were separated and the organic layer was washed twice with 1 L of 1N sodium hydroxide, dried over sodium sulfate and concentrated in vacuo to afford 140.3 g of a light yellow oil. This was distilled via Kugelrohr at 105° C. and 0.25 mm to afford 105.2 g (79.3%) of a clear liquid. The NMR was perfect for the desired product 3. A summary of the components used is provided in Table 1:

TABLE 1

| Compound | MW | moles | grams | mL |
|---|---|---|---|---|
| cinnamic acid 1 | 148.16 | 0.6749 | 100.00 | — |
| chloromethyl chlorosulfate 2 | 164.99 | 0.78 | 128.1 | — |
| tetrabutyl ammonium hydrogen sulfate | 339.54 | 0.067 | 22.9 | — |
| sodium bicarbonate | 84.01 | 2.56 | 215.5 | — |
| water | — | — | — | 700 |
| methylene chloride | — | — | — | 700 |
| 1N NaOH | — | — | — | 2000 |

N-methylbutyramide 5 was prepared as follows. Butyryl chloride 4 (25 g) was dissolved in 200 mL of ether and cooled to 0–5° C. in an ice bath. Methylamine was sparged through the reaction until no further precipitate formed. The temperature exothermed to 30.1° C. and the addition of methylamine was stopped until the temperature dropped to less than 10° C., then resumed. After about three cycles and 30 minutes, the temperature stopped rising during addition. The bath was dropped and the reaction mixture was stirred at room temperature for one hour. An aliquot was filtered, concentrated in vacuo and analyzed by NMR. The reaction was complete and very clean. The mixture was filtered and the filter cake was washed with 100 mL of THF. The combined filtrates were concentrated in vacuo to afford 21.9 g (92%) of a clear liquid; the NMR was very good. The next day, the product was distilled via Kugelrohr. A forecut was taken at 80° C. and 13 mmHg and the product distilled at 120–130° C. at 11 mmHg to afford 20.4 g (86%). The proton NMR was perfect for the desired product 5. A summary of components used is provided in Table 2.

TABLE 2

| Compound | MW | moles | grams | mL |
|---|---|---|---|---|
| butyryl chloride 4 | 106.55 | 0.23 | 25.0 | — |
| methylamine | 31 | 0.59 | 18.2 | — |
| ether | — | — | — | 200.0 |

N-methylbutyramide 5 (7.5 g) was dissolved in 40 mL of THF and 20 mL of DMSO and treated with 1.3 g of sodium hydride at 0–5° C. at which time gas evolution ceased. After stirring for 5 hours, 14.6 g of chloromethylcinnamate 3 was added in 40 mL of THF dropwise. The temperature rose from 1.2° C. to 8.8° C. and the addition took 20 minutes. The reaction mixture was stirred overnight and allowed to warm to room temperature.

The GC taken the next day showed a new product at about 15 minutes but mostly starting materials were present. The balance of the sodium hydride was added at room temperature and stirring was continued. After eight hours, there was a new product forming at 12.6 minutes as determined by GC. The GCMS indicated that this peak was the desired product with an m/e=261. The reaction was stirred overnight at room temperature.

The next day, the solution was light yellow with a heavy precipitate. TLC (1:1 hexane:ethyl acetate) indicated that the CMC 3 spot had greatly decreased and, as determined by GC, the new peak at 12.6 minutes had increased. The reaction mixture was quenched with 50 mL of water and then extracted with 100 mL of ethyl acetate. The aqueous layer was extracted with an additional 200 mL of ethyl acetate and the combined extracts were washed with 200 mL of brine, dried over sodium sulfate, filtered and concentrated in vacuo to afford 16.8 g of a light yellow oil. The NMR was perfect for the desired product plus CMC 3. The crude product was distilled via Kugelrohr up to 125° C. to remove the CMC 3 and other low boilers. The pot residue after this contained almost pure product while the distillate was primarily CMC 3.

The pot residue was chromatographed on a Biotage 75S using 85:15 hexane:ethyl acetate and the product eluted in fractions 7–21. These were concentrated in vacuo to afford 8.1 g (41.8%) of a hazy oil which was determined by proton and carbon NMRs to be perfect for the desired product 6. The product appeared as rotamers based on two sets of peaks for the N-methyl, N-methylene and α-carbonyl protons. A summary of components used is provided in Table 3.

TABLE 3

| Compound | MW | moles | grams | mL |
|---|---|---|---|---|
| N-methylbutyramide 5 | 101.15 | 0.07 | 7.5 | — |
| chloromethyl cinnamate 3 | 196.63 | 0.07 | 14.6 | — |
| sodium hydride | 24 | 0.08 | 1.9 | — |
| THF | — | — | — | 80.0 |
| DMSO | — | — | — | 20.0 |

Example 2

Preparation of N-methylcinnamamidomethyl butyrate 10

Figure 2A:
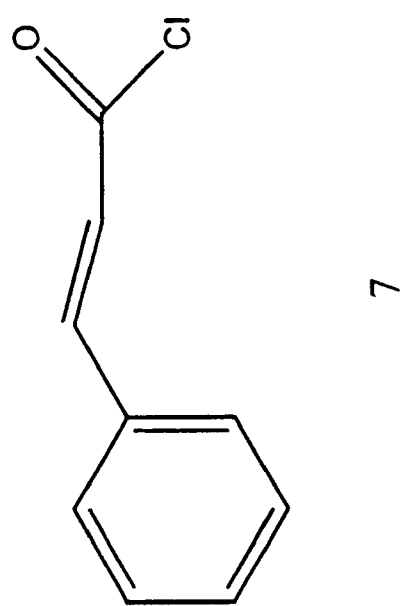
FIGS. 2A and 2B show a reaction scheme for preparing N-methylcinnamamidomethyl butyrate according to Example 2.
Figure 2A:
Figure 2A:
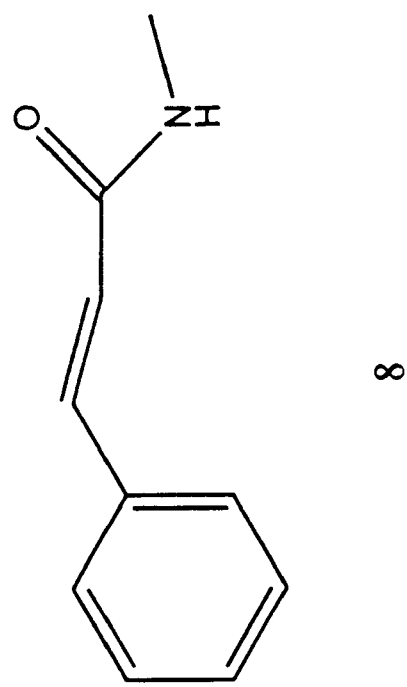
Figure 2B:
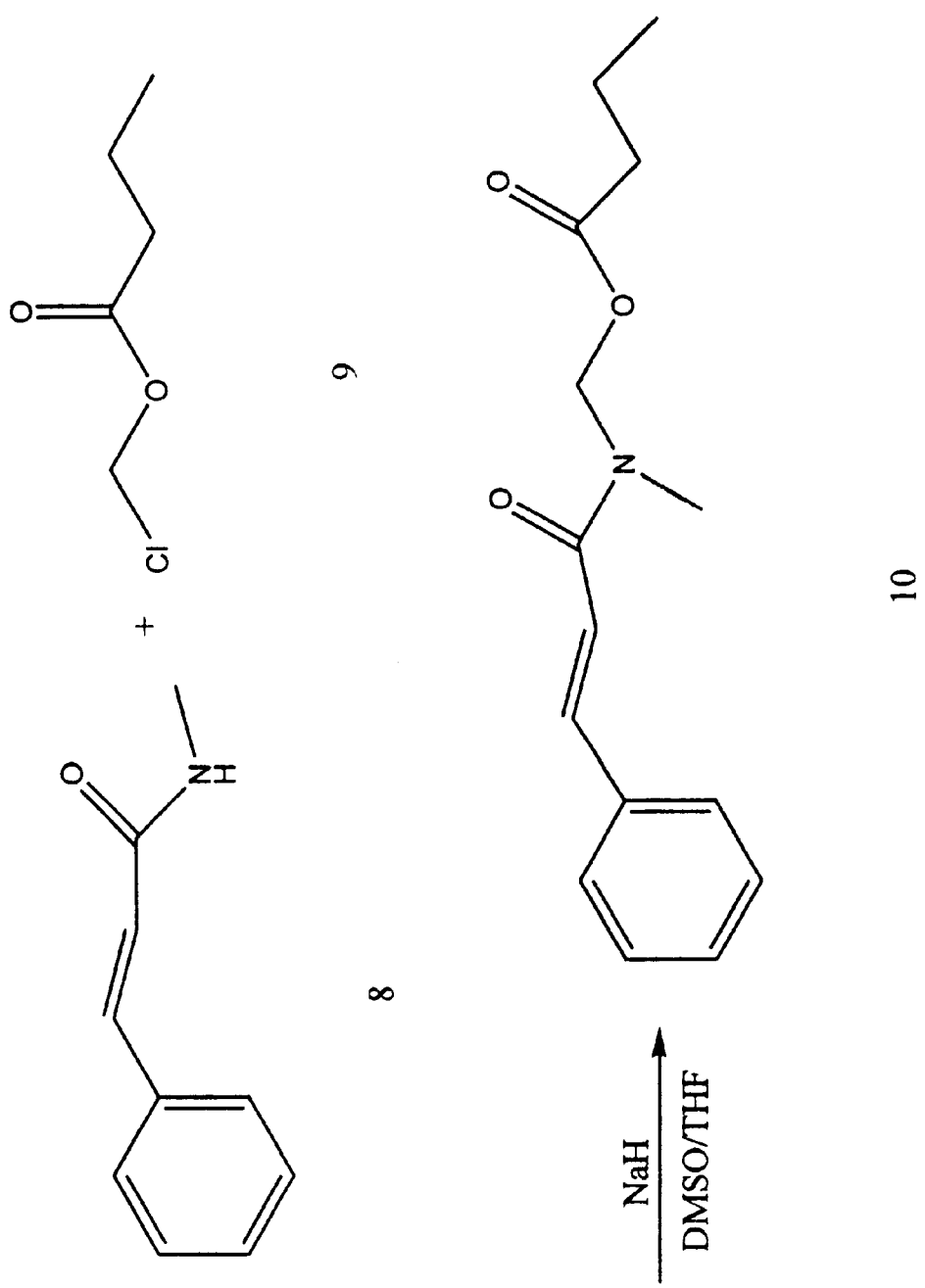
Figure 3A:
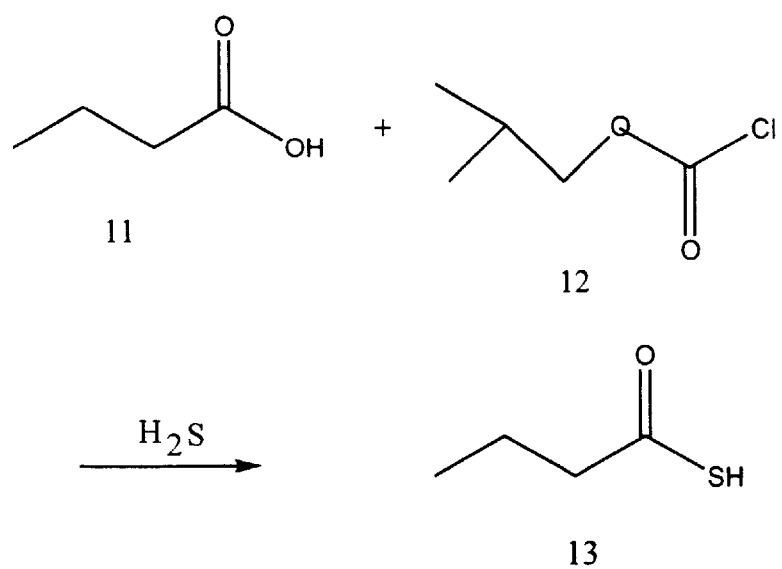
FIGS. 3A and 3B show a reaction scheme for preparing cinnamoyloxymethyl thiobutyrate and bis(thiobutyl) methane according to Example 3.
Figure 3B:
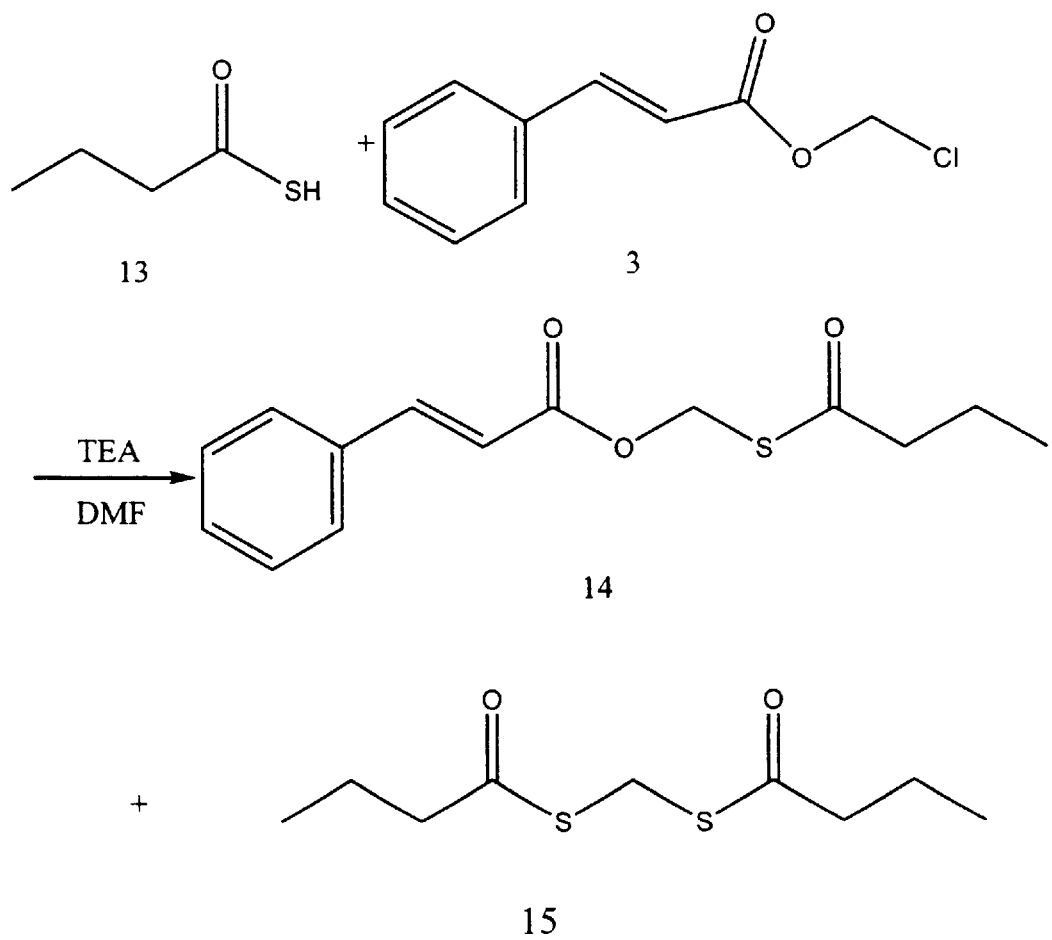
Figure 4A:
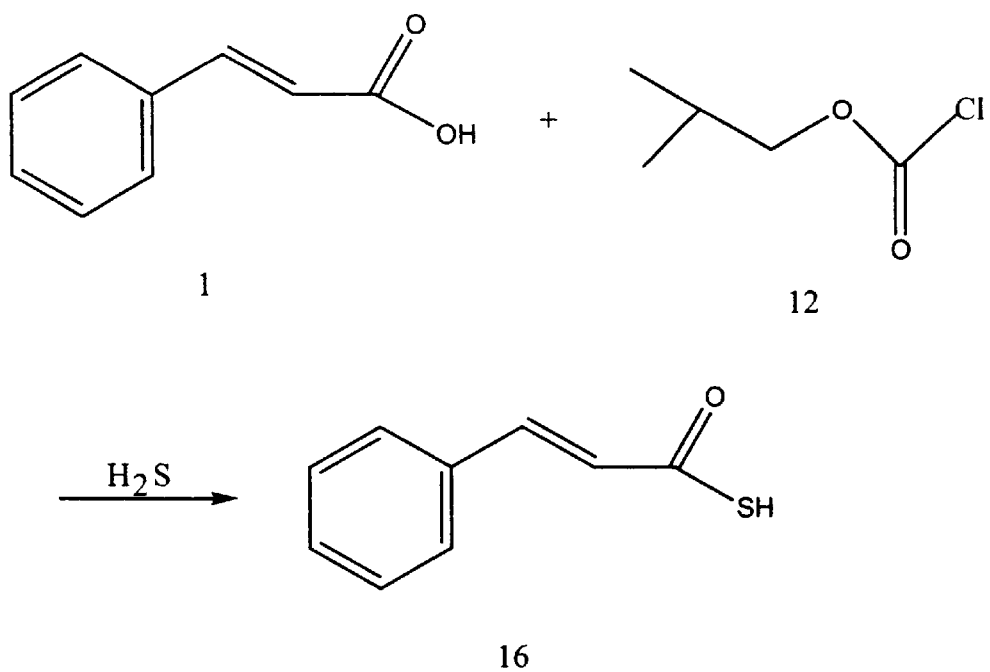
FIGS. 4A and 4B show a reaction scheme for preparing butyroyloxymethyl thiocinnamate according to Example 4.
Figure 4B:
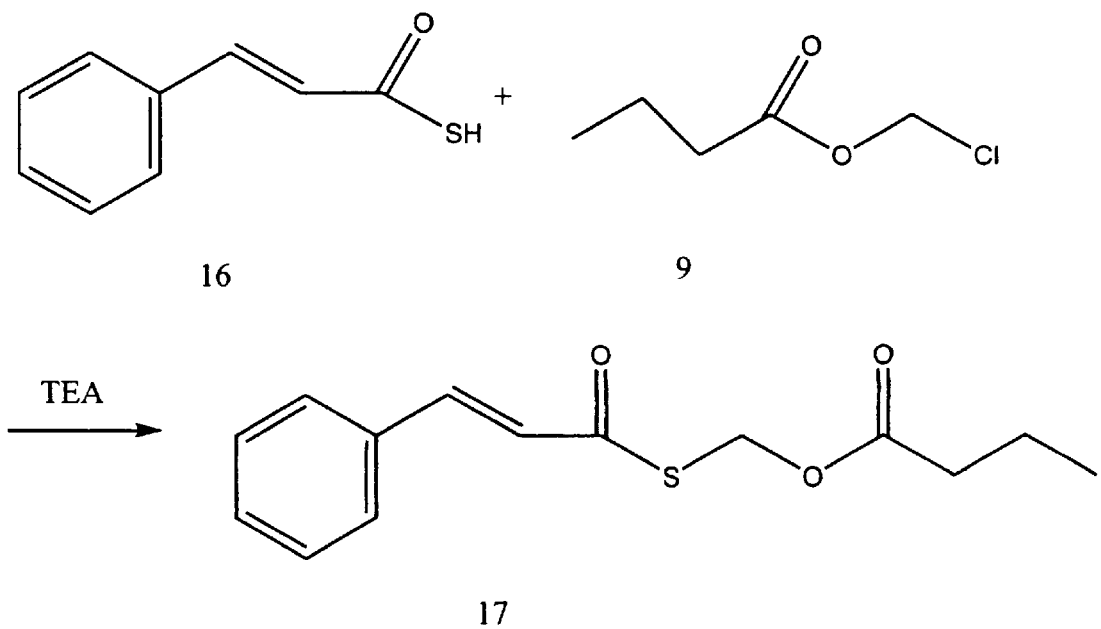

Reference numerals correspond with those in FIGS. 2A and 2B.

In the preparation of N-methylcinnamamidomethyl butyrate 10, N-methylcinnamamide 8 was first prepared. N-methylcinnamamide 8 was prepared as follows. Cinnamoyl chloride 7 (25 g) was dissolved in 200 mL of ether and cooled to 0–5° C. in an ice bath. Methylamine was sparged through the reaction mixture until no further precipitate formed. A white precipitate formed at once but the exotherm only rose to 20.4° C. After one hour the sparge was ceased and the reaction mixture was analyzed by NMR. There was no acid chloride 7 left. The reaction mixture was filtered but there was much less methylammonium chloride than expected (about one-half). The filtrate was washed with 100 mL each of saturated sodium bicarbonate and brine, dried over sodium sulfate, filtered and concentrated in vacuo to afford 28.3 g of a white solid. The NMR was perfect for the desired product 8. This was dried in vacuo to constant weight (18.3 g). The material was no longer completely soluble in chloroform or THF or water or DMSO. The bulk of the dried material was triturated with 250 mL of chloroform for one hour, filtered and the filtrate concentrated in vacuo to afford 15 g (62%) of a white solid which was determined by proton and carbon NMR to be the desired product 8. The insoluble material (2.7 g) was discarded since it could not be dissolved in any solvent for NMR analysis. A summary of the components used is provided in Table 4.

TABLE 4

| Compound | MW | moles | grams | mL |
|---|---|---|---|---|
| cinnamoyl chloride 7 | 166.6 | 0.15 | 25.0 | — |
| methylamine | 31 | 0.38 | 11.6 | — |
| ether | — | — | — | 200.0 |

A suspension of 1.2 g of sodium hydride in 20 mL of THF and 20 mL of DMSO was cooled to 0–5° C. in an ice bath and 7.5 g of N-methylcinnamamide 8 in 40 mL of anhydrous THF was added over a 30-minute period. After 30 minutes, a solution of 6.4 g of chloromethylbutyrate 9 in 20 mL of THF was added dropwise over 15 minutes. The temperature rose to 7.3° C. The bath was removed 45 minutes after the addition was complete and the resulting mixture was allowed to gradually warm room temperature. An aliquot analyzed by GC, TLC and NMR indicated that the reaction was incomplete so it was stirred overnight at room temperature.

The next day, TLC and GC indicated no real change so an additional 0.6 g of sodium hydride was added. The resulting mixture was stirred overnight again. The next day, TLC indicated not much change but GC showed the desired product was increasing. The reaction mixture was then stirred overnight again.

The following day, the reaction mixture was quenched with 100 mL of water. Ethyl acetate (100 mL) was added and the layers separated. The aqueous layer was extracted with 200 mL of ethyl acetate, dried over sodium sulfate and concentrated in vacuo to afford 11 g of a pale yellow oil which was determined by NMR to be mainly the desired product 10. This was chromatographed on a Biotage 75S and fractions 3–6 were the pure product (4.8 g). The proton and carbon NMRs were determined to be perfect for the desired product 10. GCMS gave a molecular ion of 261. CG of the final product showed it was greater than 99% pure. The product was transferred to a vial as a chloroform solution then concentrated in vacuo in situ to afford 4.7 g after Kugelrohr. A summary of the components used is provided in Table 5.

TABLE 5

| Compound | MW | moles | grams | mL |
|---|---|---|---|---|
| N-methyl cinnamide 8 | 161.2 | 0.05 | 7.5 | — |
| chloromethyl butyrate 9 | 136.6 | 0.05 | 6.4 | — |
| sodium hydride | 24 | 0.075 | 1.8 | — |
| THF | — | — | — | 80.0 |
| DMSO | — | — | — | 20.0 |

Example 3
Preparation of cinnamoyloxymethyl thiobutyrate 14 and bis(thiobutyl)methane 15

Reference numerals correspond with those of FIGS. 1A, 1B, 1C, 3A and 3B.

In the preparation of cinnamoyloxymethyl thiobutyrate 14, thiolobutyric acid 13 was first prepared as follows. Butyric acid 11 (7.5 g) was dissolved in 500 mL of methylene chloride and cooled to −15° C. in an ethylene glycol dry ice bath. TEA (25.5 mL) and isobutyl chloroformate 12 (12.1 mL) were added and the resulting solution was sparged with hydrogen sulfide for two hours at −15° C. After two hours, 42.4 g of hydrogen sulfide had been sparged through the reaction mixture. The reaction mixture was acidified with 75 mL of 2N sulfuric acid. The mixture was extracted with 400 mL of methylene chloride and the combined extracts were dried over sodium sulfate and concentrated in vacuo to afford 37.9 g of an oil. The NMR indicated a mixture of TEA•HCl, iBuOH and the TEA salt of thiolobutyric acid 13. The oil was dissolved in 100 mL of DMF and treated with 16.7 g of chloromethyl cinnamate 3, prepared as described in Example 1, in 50 mL of DMF and the resulting mixture was stirred overnight at room temperature. A GC taken immediately after addition of CMC 3 indicated that the reaction was already mostly complete.

GC analysis performed the next day indicated further conversion to the major new product. The reaction mixture was filtered and the filter cake was washed with 100 mL of ethyl acetate. The filtrates were washed with 100 mL each of 5% hydrochloric acid, saturated sodium bicarbonate and brine, dried over sodium sulfate, filtered and concentrated in vacuo to afford 20.8 g of a light yellow oil. The NMR indicated that this was mainly the desired product 14 with some CMC 3 left and another impurity at 4.25 ppm. GCMS indicated the correct m/e for the desired product 14 and the other impurity appeared to be bis(thiobutyl)methane 15 based on the m/e of 220. The product was distilled by Kugelrohr. Fraction one contained mainly CMC 3 and bis(thiobutyl)methane 15 (4.6 g, rt-110° C. @ 0.035 mmHg).

The pot residue at this point was mainly the desired product plus a small amount of CMC 3 based on the NMR. A second fraction was taken at 110–128° C. and 0.03 Torr (<1 g). After fraction two, the pot residue was mostly pure product 14 by NMR. Fraction three distilled at 130–140° C. and 0.025 Torr. It was 12.7 g (56.5%) of a light yellow oil which was determined by proton and carbon NMRs to be perfect for the desired product 14. GC analysis indicated purity of the product was greater than 99.8%. The first fraction containing CMC 3 and bis(thiobutyl)methane 15 was chromatographed on a Biotape 40M and fractions 38–66 contained the pure bis(thiobutyl)methane 15. The proton and carbon NMRs were perfect for bis(thiobutyl) methane 15. A summary of the components used is provided in Table 6.

TABLE 6

| Compound | MW | moles | grams | mL |
|---|---|---|---|---|
| butyric acid 11 | 88.11 | 0.0851 | 7.5 | — |
| isobutyl chloroformate 12 | 136.55 | 0.09 | 12.8 | 12.1 |
| TEA | 101 | 0.18 | 18.5 | 25.5 |
| methylene chloride | — | — | — | 500 |
| chloromethyl cinnamate 3 | 196.63 | 0.09 | 16.7 | — |
| DMF | — | — | — | 150 |

Example 4
Preparation of butyroyloxymethyl thiocinnamate 17

Reference numerals correspond with those of FIGS. 1A, 1B, 1C, 2A, 2B, 3A, 3B, 4A and 4B.

In the preparation of butyroyloxymethyl thiocinnamate 17, thiolocinnamic acid 16 was first prepared as follows. Cinnamic acid 1 (10 g) was dissolved in 400 mL of methylene chloride and cooled to −15° C. in an ethylene glycol dry ice bath. TEA (20.2 mL) and isobutyl chloroformate 12 (9.6 mL) were added and the resulting solution was sparged with hydrogen sulfide for two hours at −10 to −15° C. A total of 8.7 g of hydrogen sulfide was sparged through the solution. After two hours, the solution was acidified with 100 mL of 2N sulfuric acid. The mixture was extracted with 250 mL of methylene chloride and the combined extracts were dried over sodium sulfate and concentrated in vacuo to afford 14 g of an oil 16 which was determined by NMR to contain a new set of cinnamoyl olefinic peaks downfield from trans-cinnamic acid. It was also contaminated with some isobutyl alcohol. The crude thiolacid 16 was Kugelrohred in an attempt to remove the iBuOH. After heating to 35° C. at 0.05 Torr, the sample weighed 12.7 g and still contained iBuOH as determined by NMR. The putative thiolcinnamic acid 16 was dissolved in 100 mL of DMF containing 9.2 g chloromethylbutyrate 9 and TEA (11.3 mL) was added dropwise over about 10 minutes. The mixture was stirred at room temperature overnight. A precipitate began to form at once and the flask was warm, indicating a mild exotherm.

The next day, a one mL aliquot was partitioned between 1 mL each of ethyl acetate and saturated sodium bicarbonate and analyzed by TLC and GC. Both indicated that a new major product had been formed. GCMS indicated only a fragment for the thiocinnamoyl portion of the molecule. The aliquot was concentrated in vacuo and the NMR indicated that it was mainly the desired product 17. The reaction mixture was filtered and the filter cake was washed with 100 mL of ethyl acetate. The filtrate was partitioned between 100 mL each of ethyl acetate and water. The ethyl acetate layer was washed with 75 mL each of 5% hydrochloric acid, saturated sodium bicarbonate and brine, dried over sodium sulfate, filtered and concentrated in vacuo to afford 16 g of an orange oil which was determined by NMR to be perfect for the desired product 17.

The crude product was distilled via Kugelrohr. Fraction two (1.6 g, 70–140° C./0.15 Torr) contained a mixture of the desired product and cinnamoyloxymethyl butyrate. The pot after fraction was mostly the desired product by NMR. Fraction three (12.2 g, 140–160° C./0.15 Torr) was the desired product based on the proton and carbon NMRs. The GC indicated >99% purity. A summary of the components used is provided in Table 7.

TABLE 7

| Compound | MW | moles | grams | mL |
| --- | --- | --- | --- | --- |
| cinnamic acid 1 | 148.16 | 0.0675 | 10.0 | — |
| isobutyl chloroformate 12 | 136.55 | 0.07 | 10.1 | 9.6 |
| TEA | 101 | 0.15 | 14.7 | 20.2 |
| methylene chloride | — | — | — | 421.8 |
| chloromethyl butyrate 9 | 136.6 | 0.07 | 9.2 | — |
| TEA | 101 | 0.08 | 8.2 | 11.3 |
| DMF | — | — | — | 100 |

Example 5
Preparation of 3-oxohexyl cinnamate 19

Figure 5:
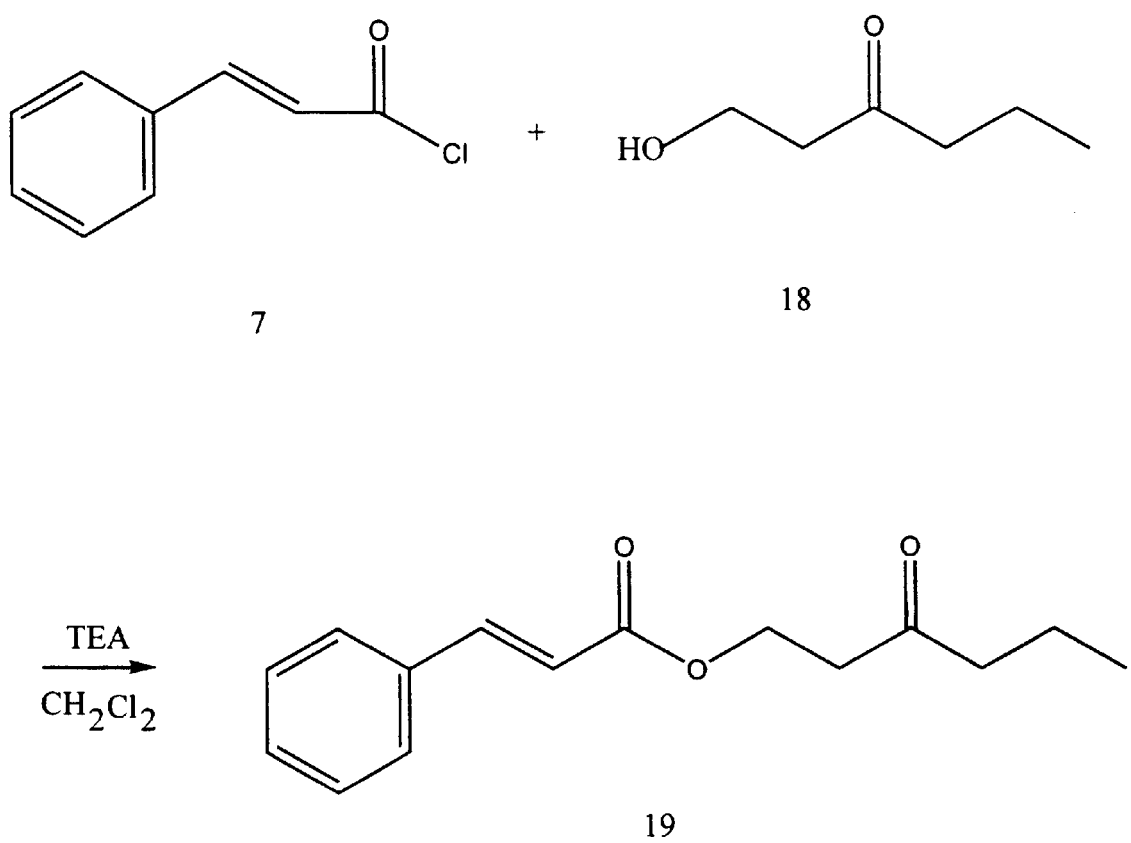
FIG. 5 shows a reaction scheme for preparing 3-oxohexyl cinnamate according to Example 5.
Figure 6A:
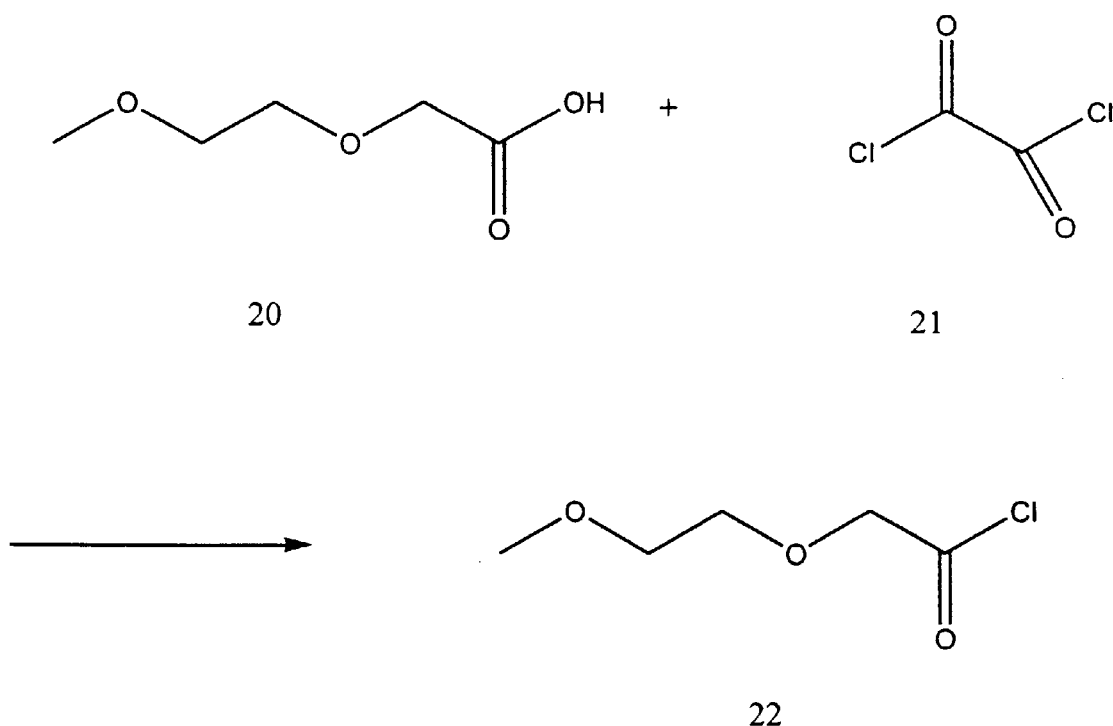
FIGS. 6A, 6B and 6C show a reaction scheme for preparing N-methyl-2-(2-methoxyethoxy)acetamidomethyl butyrate according to Example 6.
Figure 6B:
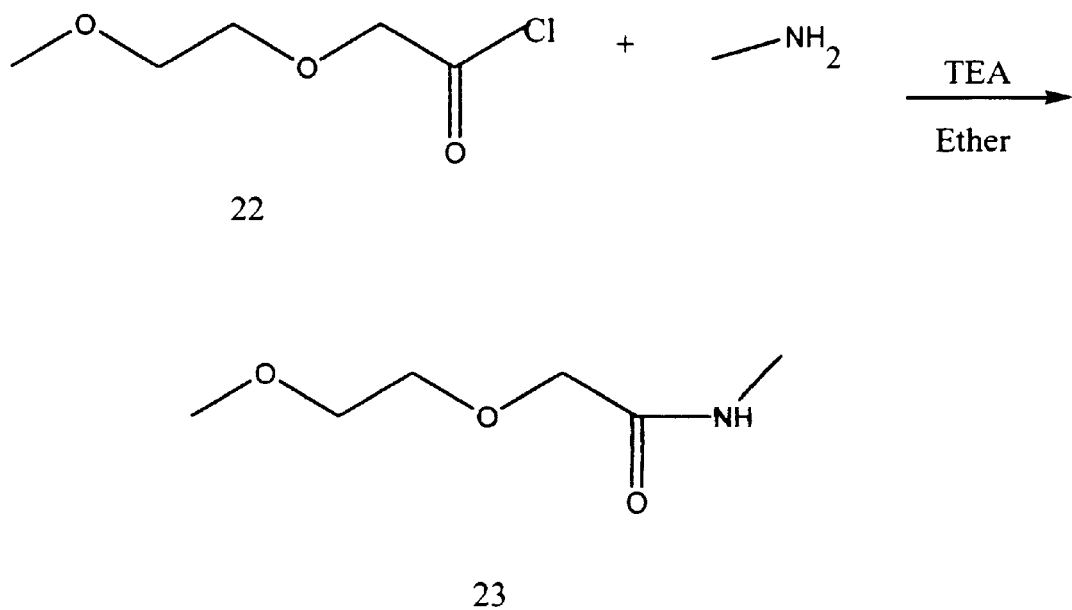
Figure 6C:
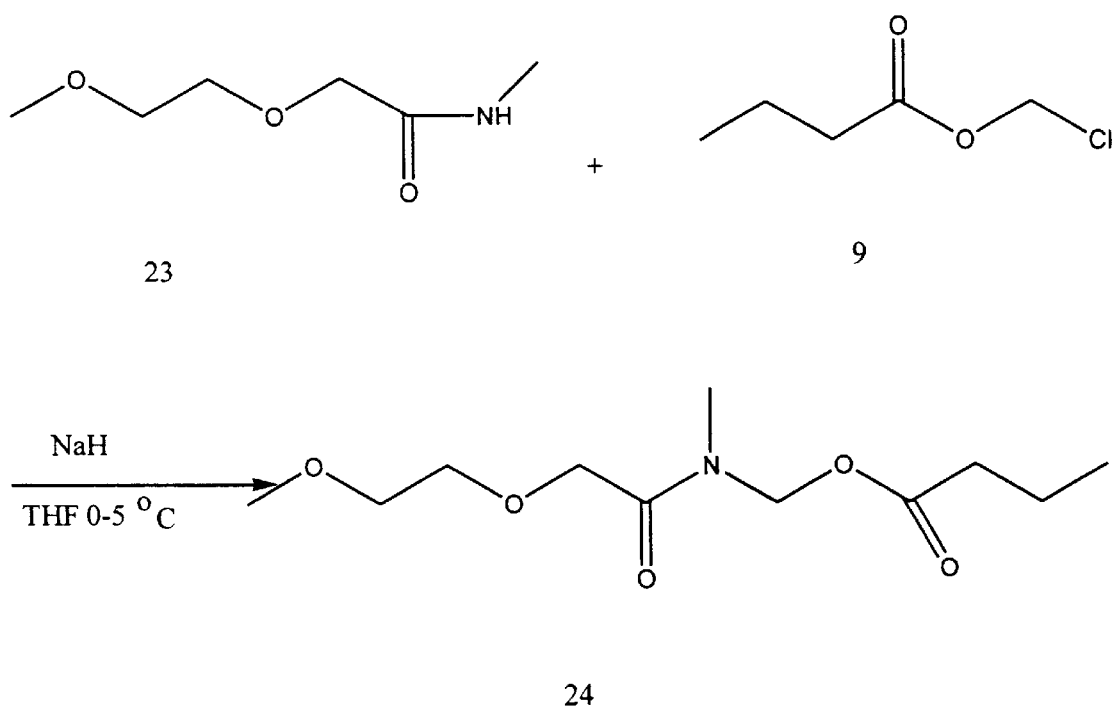
Figure 7A:
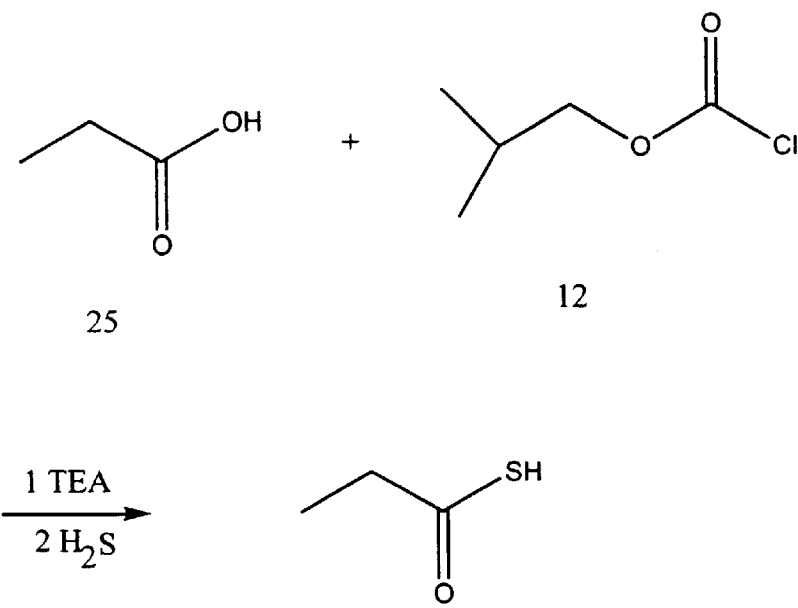
FIGS. 7A and 7B show a reaction scheme for preparing propionoyloxymethyl thiopropionate according to Example 7.
Figure 7B:
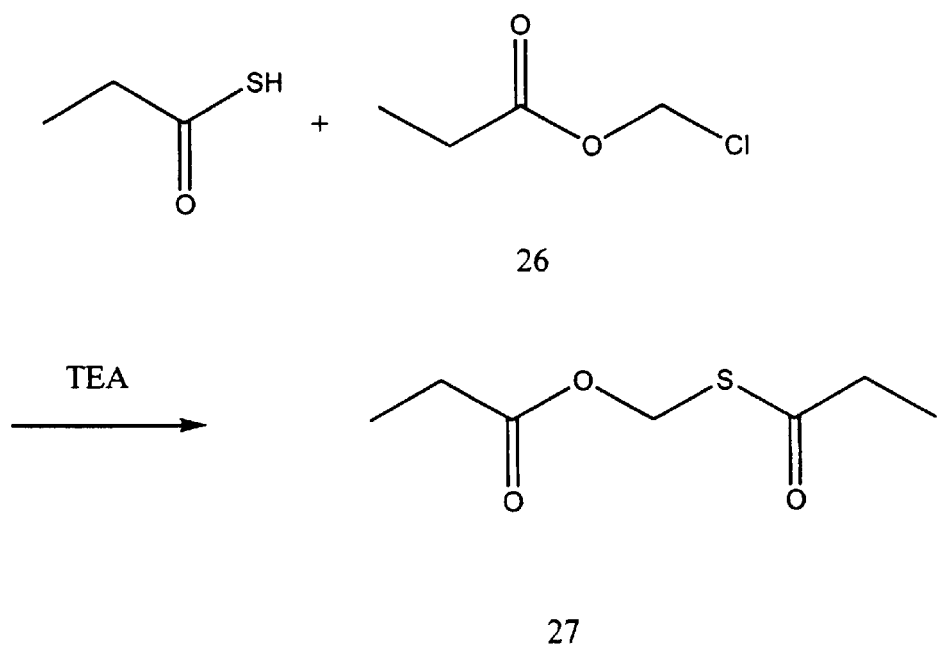

Reference numerals correspond with those of FIGS. 2A, 2B and 5.

To a solution of 3-oxohexanol 18 (7.8g) and TEA (12 mL) in 60 mL of methylene chloride at 0° C. was added a solution of cinnamoyl chloride 7 (13.5 g) in 50 mL of methylene chloride at between 0 and 5° C. After addition was completed, the resulting solution was stirred at 0 and 5° C. for additional 0.5 h and then at room temperature for 18 h. Methylene chloride and 30 mL of 3N HCl were added. The water layer was separated and extracted with methylene chloride (1×60 mL). The combined organic layers were washed with saturated sodium bicarbonate, brine, dried (MgSO$_4$) and concentrated to give a wet solid. $^1$H NMR showed two sets of doublets (vinylic protons) of equal intensities and two triplets at 4.48 and 4.35 ppm. The wet solid was triturated with hexane to give a yellow solid and the hexane filtrate was concentrated to give an orange oil. $^1$H NMR of the yellow solid showed it was mainly cinnamoyl chloride 7. $^1$H NMR of the oil showed it was the desired product 19 contaminated with cinnamoyl chloride 7 and 3-oxohexanol 18. The oil was purified on a Biotage 40M column using 10% EtOAc in hexane as an eluent. Fractions 22–53 showed one spot on TLC (15% EtOAc-hexane). Fractions 22–25 were pooled and concentrated to give a yellow oil. $^1$H NMR indicated the oil was the desired product 19 but was contaminated with ethyl acetate. $^1$H NMR of the oil from fractions 26–43 indicated the product was contaminated with cinnamoyl chloride 7. $^1$H NMR of the oil from fractions 44–53 showed no cinnamoyl chloride but had two minor triplets at 4.32 and 2.72 ppm. Hexane was added to the oil from fractions 26–43 to give a hexane solution, an immiscible oil and some solid. The mixture was stored in a refrigerator overnight.

The next day, the cold hexane solution was decanted from the oil. The oil was dissolved in 10% EtOAc in hexane. After concentraction, $^1$H NMR showed the presence of the desired product but the 10% EtOAc-hexane fraction had cinnamoyl chloride as the impurity. The oil from all fractions (except that from the 10% EtOAc-hexane fraction) were combined and concentrated at 70° C./0.3 mm for 0.5 h to give about 4.6 g of the product as a yellow oil. $^1$H NMR and C$^{13}$ NMR of the oil were consistent with the structure of the product 19. GC indicated the oil was 97.7% pure. A summary of the components used is provided in Table 8.

TABLE 8

| Compound | MW | moles | grams | mL |
| --- | --- | --- | --- | --- |
| 3-oxohexanol 18 | 116 | 0.066 | 7.8 | — |
| cinnamoyl chloride 7 | 166 | 0.08 | 13.5 | — |
| TEA | 101 | 0.086 | 8.7 | — |
| methylene chloride | — | — | — | 110 |

Example 6
Preparation of N-methyl-2-(2-methoxyethoxy) acetamidomethyl butyrate) 24

Reference numerals correspond with those of FIGS. 2A, 2B, 6A, 6B and 6C.

In the preparation of N-methyl-2-(2-methoxyethoxy) acetamidomethyl butyrate 24, 2-(2-methoxyethoxy)acetyl chloride 22 and N-methyl-2-(2-methoxyethoxy)acetamide 23 were prepared. 2-(2-methoxyethoxy)acetyl chloride 22 and N-methyl-2-(2-methoxyethoxy)acetamide 23 were prepared as follows. 2-(2-methoxyethoxy)acetic acid 20 (22.7 mL) was dissolved in 100 mL of methylene chloride containing a few drops of DMF (0.05 mL). Oxalyl chloride 21 (18.3 mL) was added dropwise and the reaction mixture was stirred overnight at room temperature.

The reaction mixture was concentrated in vacuo. The straw colored residue was concentrated in vacuo twice with 100 ml of chloroform and then pumped at high vacuum for one hour to remove any oxalyl chloride. The residue (29.9 g) was analyzed by NMR. The acid chloride 22 was dissolved in 50 mL of ether and added dropwise to 100 mL of ether, which had been sparged with methylamine to contain about 18.6 g. The reaction mixture was stirred for four hours, then filtered to remove the solid which, as determined by NMR, was methylammonium chloride. The ether layer was washed with 100 mL of 5% hydrochloric acid, twice with 100 mL of saturated sodium bicarbonate and once with 100 mL of brine. The ether layer was dried over sodium sulfate and concentrated in vacuo to afford 0.3 g which was determined by NMR to contain none of the desired product, 23.

The aqueous layer was then concentrated in vacuo and extracted with 400 mL of chloroform. The chloroform was dried over sodium sulfate and concentrated in vacuo to afford 29.2 g (99%) of a liquid which, as determined by NMR, was perfect for the desired product 23. This product was used without further purification. A summary of the components used is provided in Table 9.

TABLE 9

| Compound | MW | moles | grams | mL |
| --- | --- | --- | --- | --- |
| 2-(2-methoxy-ethoxy)acetic acid 20 | 134.13 | 0.20 | 26.8 | 22.7 |
| oxalyl chloride 21 | 126.93 | 0.21 | 26.7 | 18.3 |
| methylene chloride | — | — | — | 100 |
| DMF | — | — | — | 0.05 |
| methylamine | 31 | 0.60 | 18.6 | — |
| ether | — | — | — | 150 |

A suspension of 1.7 g of sodium hydride in 30 mL of THF was cooled to 0–5° C. in an ice bath and 10 g of N-methyl-2-(2-methoxyethoxy)acetamide 23 was added in 30 mL of anhydrous THF over a 20-minute period. After gas evolution ceased, a solution of 9.6 g of chloromethylbutyrate (CMB) 9 in 30 mL of THF was added dropwise over 15 minutes and the reaction was stirred for about two days at room temperature.

An aliquot was then analyzed by NMR and GC and the reaction was about 50% complete. An additional equivalent of CMB 9 (9.6 g) was added and the reaction was stirred overnight.

The next day, an aliquot was analyzed by NMR and GC and the reaction was about 66% complete. The reaction was terminated early by addition of 100 mL of water dropwise. An initial vigorous evolution of gas indicated that there was still sodium hydride present. Alternatively, the reaction could have been run to completion by adding 2 eq. of CMB 9 from the start and using DMSO as a co-solvent to facilitate anion formation. The aqueous layer was extracted with 100 mL of ethyl acetate and the combined organic extracts were dried over sodium sulfate and concentrated in vacuo to afford 19.7 g of a yellow liquid. The NMR was good for a mixture of both starting materials and the desired product 24. This yellow liquid was distilled via Kugelrohr. A summary of the components used is provided in Table 10.

TABLE 10

| Compound | MW | moles | grams | mL |
|---|---|---|---|---|
| N-methyl-2-methoxy ethoxy acetamide 23 | 147.17 | 0.07 | 10.0 | — |
| chloromethyl butyrate 9 | 136.6 | 0.14 | 19.2 | — |
| sodium hydride | 24 | 0.07 | 1.7 | — |
| THF | — | — | — | 120 |

Example 7

Preparation of propionoyloxymethyl thiopropionate 27

Reference numerals correspond with those of FIGS. 3A, 3B, 7A and 7B.

Propionic acid 25 (7.5 g) was dissolved in 500 mL of methylene chloride and cooled to −15° C. in an ethylene glycol dry ice bath. TEA (30.4 mL) and isobutyl chloroformate 12 (14.4 mL) were added and the resulting solution was sparged with hydrogen sulfide for two hours at −15° C. Initially a white precipitate formed but this redissolved after about 30 minutes. After two hours, 67 g of hydrogen sulfide had been sparged through the reaction mixture. The reaction mixture was concentrated in vacuo to afford an oily solid. The oily solid was dissolved in 100 mL of DMF and treated with 12.4 g of chloromethyl propionate 26 in 50 mL of DMF and the resulting mixture was stirred for 36 hours at room temperature.

An aliquot of the reaction mixture was analyzed by GC and GCMS and found to contain mainly the desired product along with small amounts of propionoyloxymethyl propionate and bis(thiopropyl)methane. The reaction was stirred an additional 24 hours.

The reaction mixture was filtered to remove TEA•HCl. The filter cake was washed with 150 mL of ethyl acetate and the filtrate was partitioned between 250 mL of water and 250 mL of ethyl acetate. The ethyl acetate extract was washed with 150 mL each of 5% hydrochloric acid, saturated sodium bicarbonate and brine, dried over sodium sulfate and concentrated in vacuo to afford 23.4 g of a yellow oil. The NMR indicated the oil contained a small amount of unreacted chloromethyl propionate 26 and some propionoyloxymethyl propionate as well as the desired product 27 and bis(thiopropyl)methane.

The reaction mixture was distilled under reduced pressure through a 10 cm Vigreaux column. Fraction one distilled at 45–110° C. and 50 mmHg and contained an equal mixture of propionoyloxymethyl propionate and propionoylmethyl thiopropionate 27 by NMR. Fraction two distilled at 110–120° C. and 20–25 mmHg. The clear liquid weighed 4.4 g and was 80–90% propionoyloxymethyl thiopropionate 27 as determined by NMR and GC. Fraction three distilled at 118–125° C. at 20–22 mmHg and contained 1.9 g of a clear liquid which by GC was 96% pure with a small amount of propionoyloxymethyl propionate and about 3% of bis(thiopropyl)methane. The proton and carbon NMRs were perfect for the desired product 27.

A summary of the components used is provided in Table 11.

TABLE 11

| Compound | MW | moles | grams | mL | Density |
|---|---|---|---|---|---|
| propionic acid 25 | 74.08 | 0.1012 | 7.50 | — | — |
| isobutyl chloroformate 12 | 136.55 | 0.11 | 15.2 | 14.4 | 1.053 |
| TEA | 101 | 0.22 | 22.0 | 30.4 | 0.726 |
| methylene chloride | — | — | — | 500 | — |
| chloromethyl propionate 25 | 122.55 | 0.10 | 12.4 | — | — |
| TEA | 101 | 0.12 | 12.3 | 16.9 | 0.726 |
| DMF | — | — | — | 100.0 | — |

Example 8

Compounds prepared according to Examples 1–7 were tested for anti-proliferation against PC-3 prostate or MCF-7 breast cancer cells. The specific compounds tested include N-methyl-2-(2-methoxyethoxy)acetamidomethyl butyrate; N-methylbutyramidomethyl cinnamate; N-methylcinnamamidomethyl butyrate; cinnamoyloxymethyl thiobutyrate; butyroyloxymethyl thiocinnamate; bis(thiobutyl)methane; 3-oxohexyl cinnamate; and propionoyloxymethyl propionate. Butyric acid and trichostatin, a potent HDAC inhibitor, were used as reference compounds. Both compounds were purchased from Sigma-Aldrich, Milwaukee, Wis.

The PC-3 cell line was maintained in RPMI supplemented with 10% fetal calf serum and antibiotics. The EDR assay was performed as described by Kern and Weisenthal in "Highly Specific Prediction of Antineoplastic Drug Resistance With An In Vitro Assay Using Suprapharmacologic Drug Exposures," *J. Nat. Cancer Inst.*, 82:582–588 (1990); and Fruehauf and Bosanquet, "In vitro Determination of Drug Response: A Discussion of Clinical Applications," PPO Updates 7(12):1–16 (1993). Cells were suspended in 0.12% soft agar in complete medium and plated (2,000 cells per well, as determined by preliminary experiments) in different drug concentrations onto a 0.4% agarose underlayer in 24-well plates. Plating cells on agarose underlayers supports the proliferation only of the transformed cells, ensuring that the growth signal stems from the malignant component of the tumor.

All compounds were dissolved in DMSO to 200× stock solutions. Stock solutions were diluted to 20× working solutions using the tissue culture medium, serially diluted and added to the 24-well plates. The concentration range was 0.001 $\mu$M to 0.3 $\mu$M for trichostatin and 10 $\mu$M–1,000 $\mu$M for the other compounds. No significant changes in pH of the culture medium were observed under the above conditions. Diluent control wells contained PC3 cells treated with DMSO, at the dilutions used for appropriate drug treatment. All experimental points were represented by two separate wells (duplicates). Positive controls were determined using at least two wells treated with an extremely high dose of cisplatin, an anti-cancer agent. Four wells containing tumor cells that were not treated with drugs served as negative controls in each experiment.

Cells were incubated with drugs under standard culture conditions for five days. Cultures were pulsed with tritiated thymidine ($^3$H-TdR, New Life Science Products, Boston, MA) at 5 µCi per well for the last 48 hours of the culture period. Cell culture plates were then heated to 90° C. to liquefy the agarose, and cells were harvested onto glass fiber filters, which were then placed into counting vials containing liquid scintillation fluid. The radioactivity trapped on the filters was counted with a Beckman scintillation counter. The fraction of surviving cells was determined by comparing $^3$H-TdR incorporation in treated (experimental points) and untreated (negative control) wells. All drug concentrations are presented as µM, allowing for normalization of drug response curves and direct comparison of the effects of the drugs. Microsoft Excel was used to organize the raw data on EDR experiments, and the SigmaPlot program was utilized to generate drug response curves. All drug response curves were as approximated as sigmoidal equations (characteristic for typical drug response curves) to fit the data. $IC_{50}$ values were determined using the approximated sigmoidal curves and expressed as µM. Table 12 provides the PC-3 or MCF-7 $IC_{50}$ data for each of the compounds tested.

TABLE 12

| COMPOUND | PC-3 or MCF-7* $IC_{50}$ (µM) |
| --- | --- |
| N-methyl-2-(2-methoxyethoxy)acetamidomethyl butyrate | 36 |
| N-methylbutyramidomethyl cinnamate | 100 |
| N-methylcinnamamidomethyl butyrate | 20 |
| cinnamoyloxymethyl thio-butyrate | 30 |
| butyroyloxymethyl thiocinnamate | 30 |
| bis(thiobutyl)methane | 40 |
| propionoyloxymethyl thiopropionate | 50* |
| 3-oxohexyl cinnamate | 40 |
| butyric acid | >2000 |
| trichostatin | 0.005 |

*This value was obtained from MCF-7 cell line.

As can be seen from Table 12, the results demonstrate that the dicarbonyl compounds of the present invention possess superior activity as compared to butyric acid.

Whereas particular embodiments of this invention have been described above for purposes of illustration, it will be evident to those skilled in the art that numerous variations of the details of the present invention may be made without departing from the invention as defined in the appended claims.

What is claimed is:

1. A compound having the formula (1):

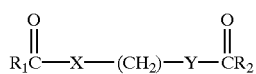 (1)

wherein X is selected from the group consisting of oxygen, sulfur and N(R);
wherein Y is sulfur;
wherein R is either H or $CH_3$;
wherein $R_1$ and $R_2$ are the same or different and have the general formula (2);

 (2)

wherein $R_3$ and $R_4$ are the same or different and are selected from the group (CH=CH), (C C), sulfur and oxygen;
wherein Z is selected from the group consisting of hydrogen and substituted or unsubstituted aryl, heteroaryl, cycloalkyl having the formula $C_nH_{2n-1}$ and alkoxy;
wherein n is 3 or greater; and
wherein o, p, q, r and s are the same or different and are each between 0 and 10, o+q+s being greater than or equal to 2 when both p and r are 0.

2. The compound of claim 1, wherein Z is substituted with one or more members of the group consisting of halogen, hydroxy, alkyl, alkoxy, cyano, amino, nitro, carbonyl, and halogenated hydrocarbon groups, and when more than one substituents are present they can be the same or different.

3. The compound of claim 1, wherein $R_1$ and $R_2$ are the same or different and are selected from the group consisting of $CH_2CH_3$; $CH_2CH_2CH_3$; and $CH_2CH_2CH_2CH_3$.

4. The compound of claim 1, wherein both X and Y are sulfur and both $R_1$ and $R_2$ are $CH_2CH_2CH_3$.

5. The compound of claim 1, wherein both X and Y are sulfur and both $R_1$ and $R_2$ are $CH_2CH_3$.

6. A compound having the formula (1):

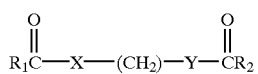 (1)

wherein X is selected from the group consisting of oxygen, sulfur and N(R);
wherein Y is selected from the group consisting of sulfur, N(R), and $CH_2$;
wherein R is either H or $CH_3$;
wherein $R_1$ and $R_2$ are the same or different, each include at least two carbon atoms, and have the general formula (2);

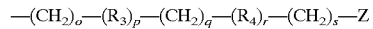 (2)

wherein $R_3$ and $R_4$ are the same or different and are selected from the group (CH=CH), (C≡C), sulfur and oxygen;
wherein Z is selected from the group consisting of hydrogen and substituted or unsubstituted aryl, heteroaryl, cycloalkyl having the formula $C_nH_{2n-1}$ and alkoxy;
wherein n is 3 or greater; and
wherein o, p, q, r and s are the same or different and are each between 0 and 10 and when X is oxygen and Y is N(R), at least one p is between 1 and 10, when X is sulfur and Y is sulfur, at least one o, p, q, r and s is between 1 and 10, and when X is oxygen and Y is $CH_2$, Z is selected from the group consisting of hydrogen, unsubstituted aryl, substituted or unsubstituted heteroaryl, substituted or unsubstituted cycloalkyl having the formula $C_nH_{2n-1}$, and substituted or unsubstituted alkoxy, and o+q+s are greater than 2 when both p and r are 0.

7. The compound of claim 6, wherein X is oxygen, Y is N($CH_3$), one of $R_1$ or $R_2$ is $CH_2CH_2CH_3$, and the other of $R_1$ or $R_2$ is —CH=CH—$C_6H_5$.

8. The compound of claim 6, wherein X is oxygen, Y is sulfur, one of $R_1$ or $R_2$ is $CH_2CH_2CH_3$, and the other of $R_1$ or $R_2$ is —CH=CH—$C_6H_5$.

9. The compound of claim 6, wherein X is oxygen, Y is $CH_2$, $R_1$ is —CH=CH—$C_6H_5$, and $R_2$ is $CH_2CH_2CH_3$.

10. The compound of claim 6, wherein X is oxygen, Y is $N(CH_3)$, $R_1$ is $CH_2CH_2CH_3$ and $R_2$ is $CH_2OCH_2CH_2OCH_3$.

11. A compound having the formula (1):

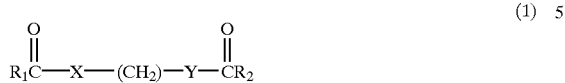 (1)

wherein X is selected from the group consisting of oxygen, sulfur and N(R);

wherein Y is selected from the group consisting of sulfur and N(R);

wherein R is either H or $CH_3$;

wherein $R_1$ and $R_2$ are the same or different, each include at least two carbon atoms, and have the general formula (2);

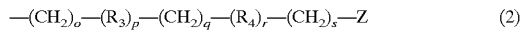 (2)

wherein $R_3$ and $R_4$ are the same or different and are selected from the group (CH=CH), (C≡C), sulfur and oxygen;

wherein Z is selected from the group consisting of hydrogen, substituted aryl, substituted or unsubstituted heteroaryl, substituted or unsubstituted cycloalkyl having the formula $C_nH_{2n-1}$ and substituted or unsubstituted alkoxy;

wherein n is 3 or greater; and wherein o, p, q, r and s are the same or different and are each between 0 and 10, and o+q+s are greater than 3 when X is oxygen, Y is $N(CH_3)$ and both p and r are 0.

12. The compound of claim 11, wherein X is oxygen and Y is $N(CH_3)$.

* * * * *